United States Patent [19]

Gaffney et al.

[11] Patent Number: 4,795,849

[45] Date of Patent: Jan. 3, 1989

[54] METHANE CONVERSION PROCESS

[75] Inventors: Ann M. Gaffney, West Chester; C. Andrew Jones, Newtown Square; John A. Sofranko, West Chester, all of Pa.

[73] Assignee: Atlantic Richfield Company, Los Angeles, Calif.

[21] Appl. No.: 236,294

[22] Filed: Aug. 23, 1988

Related U.S. Application Data

[63] Continuation of Ser. No. 81,508, Aug. 4, 1987, abandoned.

[51] Int. Cl.$^4$ .................................................. C07C 2/00
[52] U.S. Cl. ...................................... 585/500; 585/415; 585/417; 585/418; 585/541; 585/654; 585/656; 585/658; 585/661; 585/943
[58] Field of Search ............... 585/415, 500, 400, 417, 585/541, 700, 943, 418, 654, 656, 661

[56] References Cited

U.S. PATENT DOCUMENTS

| | | | |
|---|---|---|---|
| 4,450,310 | 5/1984 | Fox et al. | 585/400 |
| 4,523,050 | 6/1985 | Jones et al. | 585/500 |
| 4,544,784 | 10/1985 | Sofranko et al. | 585/500 |
| 4,544,785 | 10/1985 | Withers et al. | 585/500 |
| 4,547,611 | 10/1985 | Jones et al. | 585/500 |
| 4,574,038 | 3/1986 | Wan | 585/500 |
| 4,593,139 | 6/1986 | Withers | 585/500 |
| 4,613,718 | 9/1986 | Jaecker et al. | 585/500 |

OTHER PUBLICATIONS

Hinsen et al., Chemiker-Zeitung, vol. 107, pp. 223–226 (1983).

*Primary Examiner*—A. Pal
*Attorney, Agent, or Firm*—William C. Long

[57] ABSTRACT

Methane is converted to higher hydrocarbons by contact with a catalyst comprised of a reducible metal oxide which had previously been treated with a reducing agent such as hydrogen to improve characteristics of the catalyst.

11 Claims, No Drawings

METHANE CONVERSION PROCESS

This is a continuation application of applicants' application Ser. No. 07/081,508 filed Aug. 4, 1987, now abandoned.

BACKGROUND OF THE INVENTION

This invention relates to the conversion of methane to higher hydrocarbons. A particular application of this invention is a method for converting natural gas to more readily transportable material.

Methane can be converted to higher hydrocarbons by reaction at conditions of elevated temperature—e.g. a temperature selected within the range from about 500° C. to about 1000° C. For example, methane can be contacted with an oxidative synthesizing agent containing a reducible metal oxide at such elevated temperatures in order to produce higher hydrocarbons. Reducible oxides of several metals have been identified which are capable of converting methane to higher hydrocarbons. In particular, oxides of manganese, tin, indium, germanium, lead, antimony, bismuth, praseodymium, terbium, cerium, iron and ruthernium are most useful. See commonly-assigned U.S. Pat. Nos. 4,443,644 (Sb); 4,443,649 (Mn); 4,444,984 (Sn); 4,445,648 (In); 4,443,645 (Ge); 4,443,674 (Pb); 4,443,646 (Bi); 4,499.323 (Pr); 4,499,324 (Ce); and 4,593,139 (Ru), the entire contents of which are incorporated herein by reference. See also commonly-assigned U.S. patent application Ser. No. 06/666,694 (Fe) now U.S. Pat. No. 4,721,828 the entire content of which is incorporated herein by reference.

Commonly-assigned U.S. Pat. No. 4,554,395 discloses and claims a process which comprises contacting methane with an oxidative synthesizing agent under elevated pressure (2-100 atmospheres) to produce greater amounts of $C_2+$ hydrocarbon products.

Commonly-assigned U.S. Pat. No. 4,560,821 discloses and claims a process for the conversion of methane to higher hydrocarbons which comprises contacting methane with particles comprising an oxidative synthesizing agent which particles recirculate between two physically separate zones—a methane contact zone and an oxygen contact zone.

U.S. Pat. No. 4,499,322 discloses and claims a process for the conversion of methane to higher hydrocarbon and comprises contacting methane with an oxidative synthesizing agent containing a promoting amount of alkali metal and/or compounds thereof.

U.S. Pat. No. 4,495,374 discloses and claims a process for the conversion of methane to higher hydrocarbons which comprises contacting methane with an oxidative synthesizing agent containing a promoting amount of alkaline earth metal and/or compounds thereof.

Hinsen and Baerns report studies of a continuous mode for the oxidative coupling of methane wherein regeneration air is cofed with methane feed. Hinsen, W. and Baerns, M., "Oxidative Koppling von Methan zu $C_2$— Kohlenwasserstoffen in Gegenwart unterschiedlicher Katalsatoren", Chemiker-Zeitung, Vol. 107, No. 718, pp. 223-226 (1983). Using a catalyst based on lead oxide and gamma-alumina in a fixed bed reactor operated at 1 atmosphere total pressure and 600-750 degrees C., they report results of approximately 53% selectivity to ethane and ethylene at 8% methane conversion for a feed consisting of about 50% methane, 25% air and 25% nitrogen. Other metal oxides studied by Hinsen and Baerns included oxides of Bi, Sb, Sn and Mn.

U.S. Pat. No. 4,523,049, discloses and claims a process for converting methane to higher hydrocarbons which comprises contacting methane and an oxygen-containing gas with a solid comprising a reducible metal oxide and an alkali/alkaline earth metal promotor.

U.S. Pat. No. 4,523,050 discloses and claims a process for converting methane to higher hydrocarbons which comprises contacting methane and an oxygen-containing gas with a manganese silicate.

Commonly-assigned copending U.S. patent application Ser. No. 07/014406 filed Feb. 13, 1987 discloses and claims a method for converting methane to higher hydrocarbons wherein methane and added water are contacted in the substantial absence of added gaseous oxidant with a solid comprising at least one reducible metal oxide.

Commonly-assigned copending U.S. patent application Ser. No. 07/014405 filed Feb. 13, 1987 discloses and claims a method for converting methane to higher hydrocarbons wherein methane and a gaseous oxidant together with added water are contacted with a non acidic solid and/or a reducible metal oxide.

The reaction products of the foregoing processes are hydrocarbons, carbon oxides, coke and water.

The methane conversion reaction can be carried out by contacting methane with the reducible metal oxide in the fluidized bed reaction systems as well as in fixed bed systems.

A problem in the past has been that the catalysts employed have not had entirely satisfactory characteristics of fluidity, strength, density, attrition resistance and heat conductivity while also possessing appropriate oxygen transfer activity.

SUMMARY OF THE INVENTION

It has now been found that the fluidity, strength, density, attrition resistance and heat transfer of the reducible metal oxide catalyst can be substantially improved while still retaining suitable oxygen transfer properties, by subjecting the catalyst to treatment with a reducing agent prior to use in the methane conversion reaction.

DETAILED DESCRIPTION OF THE INVENTION

The present invention is applicable to processes of the "redox" type where methane is contacted with a reducible metal oxide in the substantial absence of gaseous oxidant and the reduced metal oxide is regenerated in a separate oxidizing step, as well as to processes of the "cofeed" type where gaseous oxidant is incorporated with methane in the gaseous feed to the reaction system. In an especially preferred practice, a promoting amount of halide material is used in the reaction system.

In one embodiment of the invention, methane is converted to higher hydrocarbons by contact at reactive conditions with a reducible metal oxide oxidative synthesizing agent which has been treated with a reducing agent. This contact can be carried out in the "redox" mode wherein methane is contacted with the reducible oxide in the absence of added gaseous oxidant and subsequently the reduced oxide is oxidized by contact with oxidant gas in the substantial absence of methane. See, for example, U.S. Pat. Nos. 4,443,649, 4,444,984, 4,445,648, 4,443,645, 4,443,674, 4,443,646, 4,499,323, 4,499,324 and 4,593,139 for an extensive description of this mode of operation.

Alternatively, the invention can be practiced by contacting a mixture of methane and gaseous oxidant in the "cofeed mode" at reactive conditions with a reducible metal oxide containing contact solid which has been treated with a reducing agent.

There are a number of important considerations in connection with the reducing agent treatment of the reducible metal oxide catalyst. It is essential that the treatment not be so severe that the oxygen transfer capability of the catalyst is reduced to a level where the catalyst can no longer be effectively used in the methane conversion reaction. However, the treatment must be sufficient to substantially improve the important catalyst charactertistics of fluidity, strength, attrition resistance, density and heat conductivity.

Gaseous reducing agents which are employed include hydrogen, methane, hydrogen sulfide, carbon monoxide, ammonia, ethane and other alkanes, and the like of which hydrogen is the preferred treating agent.

Solid reducing agents which can be employed include carbonaceous materials such as coal, coke, and the like. Organic $C_1$—$C_{12}$ acids and aldehydes such as formic acid can be emlpoyed. Sodium and lithium borohydrides can be used as well as other common organic and inorganic reducing agents.

Treatment of the catalyst with the reducing agent is carried out at elevated temperature. Generally temperatures ranging from 650° C. to about 1200° C., preferably 850° C. to 1000° C. are used. Treatment times in the range of 1 second to 24 hours, preferably 1 minute to 5 hours are appropriate. In general, the reducing agent treatment is continued until the catalyst is significantly improved in the desired properties while still retaining satisfactory oxygen transfer capability.

In particular, it is advantageous to carry out the reducing agent treatment such that the catalyst is contacted with at least the stoichiometric amount of reducing agent necessary to reduce the metal oxide to a lower oxide state. Preferably 0.5-20 times the stoichiometric quantity of the reducing agent is employed.

Desirably, after completion of the treatment with reducing agent and before use in the methane conversion reaction, the reducible metal oxide catalyst is first reoxidized in order to restore activity. For best results, the reoxidation should be carried out under mild conditions to prevent overheating and damage to the catalyst.

The catalyst may be reoxidized at temperatures ranging from 350° C. to 1200° C., preferably 500° C. to 1000° C. During reoxidation the oxidant, eg. $O_2$, may be diluted with inerts such as nitrogen to avoid excessive temperature excursions due to the exothermicity of the reaction. Most desirably the catalyst temperature is not permitted to go above about 850° C. during reoxidation.

The treated catalyst, improved in fluidity, strength, density, attrition resistance and heat conductivity, is then used in the conversion of methane to higher hydrocarbons.

With regard to reducible metal oxides, while such solids are sometimes referred to as "catalysts" it will be understood that, under conditions of use, nonacidic solids comprising a reducible metal oxide act a selective oxidants, and, therefore, take on the characteristics of a reactant during use. Thus, for example, the term "Mn-containing oxides" is meant to embrace both reducible oxides of Mn and reduced oxides of Mn, it being understood reducible oxides comprise the principal active component of the compositions.

In their active state, such catalysts comprise at least one reducible oxide of at least one metal, which oxide when contacted with methane at synthesizing conditions (e.g, at a temperature within the range of about 500° to 1000° C.) produces higher hydrocarbon products, coproduct water, and a reduced metal oxide. The term "reducible" is used to identify those oxides of metals which are reduced under the aforesaid conditions. The term "reducible oxides of metals" includes: (1) compounds described by the general formula $M_xO_y$ wherein M is a metal and x and y designate the relative atomic proportions of metal and oxygen in the composition and/or (2) one or more oxygen-containing metal compounds (i.e., compounds containing elements in addition to the metal and O), provided that such oxides and compounds have the capability of producing higher hydrocarbon products from methane as described herein.

Effective agents for the conversion of methane to higher hydrocarbons have previously been found to comprise reducible oxides of metals selected from the group consisting of manganese, tin, indium, germanium, antimony, lead, bismuth and mixtures thereof. See U.S. Pat. Nos. 4,443,649; 4,444,984; 4,443,648; 4,443,645; 4,443,647; 4,443,644; and 4,443,646. Reducible oxides of manganese are particularly preferred catalyst components.

Reducible oxides of cerium, praseodymium, and terbium have also been found to be effective for the conversion of methane to higher hydrocarbons, particularly associated with an alkali metal component and/or an alkaline earth metal component. See U.S. Pat. Nos. 4,499,324 (Ce) and 4,499,323 (Pr) and also see commonly-assigned U.S. patent application Ser. No. 06/600,918 (Tb) now abandoned.

Reducible oxides of iron and ruthenium are also effective, particularly when assoicated with an alkali or alkaline earth component. See commonly-assigned U.S. patent application 06/600,730 (Fe) now abandoned and U.S. Pat. Nos. 4,489,215 and 4,593,139 (Ru).

Alkali and alkaline earth metals and compounds thereof have been found to improve the hydrocarbon product selectivity of reducible metal oxides. The further incorporation of phosphorous into solids promoted by alkali or alkaline earth components enhances catalyst stability. See commonly-assigned U.S. Pat. Nos. 4,499,322 and 4,495,374, the entire content of which are incorporated herein by reference. Alkali metals are selected from the group consisting of lithium, sodium, potassium, rubidium and cesium. Lithium, sodium and potassium, and especially lithium and sodium, are preferred alkali metals. Alkaline earth metals are selected from the group consisting of magnesium, calcium, strontium and barium. Presently preferred members of this group are magnesium and calcium. Compositions derived from magnesia have been found to be particularly effective catalyst materials. Boron and compounds thereof are also desirably present in the reducible metal oxide catalyst employed in the process of this invention. See commonly-assigned copending U.S. patent application Ser. No. 06/877,574, the entire content of which is incorporated herein by reference. One class of boron-promoted compositions useful in the process of this invention comprises:

(1) at least one reducible metal oxide,
(2) at least one member of the group consisting of boron and compounds thereof, and (3) at least one member of the group consisting of oxides of alkaline earth metals.

A related class of catalyst compositions further comprises at least one alkali metal or compound thereof. Sodium and lithium are preferred alkali metal components.

One further, special class of catalyst compositions useful in the process of this invention are mixed oxides of sodium, magnesium, manganese and boron characterized by the presence of the crystalline compound $NaB_2Mg_4Mn_2O_x$ wherein x is the number of oxygen atoms required by the valence states of the other elements, said compound having a distinguishing x-ray diffraction pattern. In its most active form, the compound is believed to correspond to the formula $NaB_2Mg_4Mn_2O_{11}$. While this crystalline compound has been found to be associated with highly effective oxidant compositions, it has further been found that still better results are obtained when the oxidant is characterized by both: (1) the presence of crystalline compound $NaB_2Mg_4Mn_2O_x$ and (2) a stoichiometric excess of Mn relative to at least one of the other elements of the crystalline compound. In currently preferred oxidants of this type, a stoichiometric excess of Mn relative to B is provided. In a still more specific preferred embodiment excess amounts of Na and Mg, as well as Mn, are present in the mixed oxide composition relative to the amounts required by the amount of boron present to satisfy the stoichiometry of the compound $NaB_2Mg_4Mn_2O_x$.

Further examples of components which may be present in the catalysts used in the process of this invention are halogen and chalcogen components. Such components may be added either during preparation of the catalysts or during use. Methane conversion processes employing halogen-promoted reducible metal oxides are disclosed in U.S. Pat. No. 4,544,784. Methane conversion processes employing chalcogen-promoted, reducible metal oxides are disclosed in U.S. Pat. No. 4,544,785.

The reducible metal oxides compositions may be supported by or diluted with support materials such as silica, alumina, titania, zirconia and the like, and combinations thereof. When supports are employed, alkaline earth oxides, especially magnesia, are preferred.

The catalysts are conveniently prepared by any of the methods associated with similar compositions known in the art. Thus, such methods as precipitation, co-precipitation, impregnating, granulation, spray drying or dry-mixing can be used. Supported solids may be prepared by methods such as adsorption, impregnation, precipitation, co-precipitation, and dry-mixing. For example, compounds of Mn,Sn,In,Ge,Pb,Sb,Bi,Pr,Tb,Ce,Fe and/or Ru may be combined with compounds of other components in any suitable way. Substantially any compound of the components can be employed. Compounds typically used would be oxides or organic or inorganic salts of the recited components.

To illustrate, when preparing a catalyst containing: (1) a reducible metal oxide component (e.g., Mn), (2) an alkali metal component, (3) a boron component and (4) an alkaline earth component; one suitable method of preparation is to impregnate compounds of the fourth component of the composition with solutions of compounds of Mn, alkali metals, and/or boron. Suitable compounds for impregnation include the acetates, acetyl acetonates, oxides, carbides, carbonates, hydroxides, formates, oxalates, nitrates, phosphates, sulfates, sulfides, tartrates, fluorides, chlorides, bromides, or iodides. After impregnation the preparation is dried to remove solvent and the dried solid is calcined at a temperature selected within the range of about 300° to 1200° C. Particular calcination temperatures will vary depending on the compounds employed. Preferably, the alkaline earth component is provided as the oxide. Preferably, the alkali metal component is provided as a basic composition of the alkali metal(s). Examples are sodium hydroxide, sodium acetate, lithium hydroxide, lithium acetate, etc. When P is employed as an additive, it has been found desirable to add the alkali metal and P to the composition as compounds such as the orthophosphates, metaphosphates, and pyrophosphates of alkali metals. Pyrophosphates are preferred. Sodium pyrophosphate is particularly preferred. Preferably, the boron component is provided as boric acid, boric oxide (or anhydride), alkali metal borates, boranes, borohydrides, etc., especially boric acid or oxide.

Formation of the crystalline compound $NaB_2Mg_4Mn_2O_x$ may be accomplished by reacting active compounds of the substituent elements. A suitable mixture of the reactive compounds is formed and heated for a time sufficient to form the crystalline material. Typically, a temperature of about 850° to about 950° C. is sufficient. When preparing mixed oxide compositions characterized by the presence of other crystalline compounds, the composition is desirably incorporated with binders or matrix materials such as silica, alumina, titania, zirconia, magnesia and the like.

Regardless of which particular catalyst is prepared or how the components are combined, the resulting composite will generally be dried and may or may not be calcined at elevated temperatures prior to the reducing agent treatment of the present invention.

Preferably, methane is contacted with reducible metal oxides in the substantial absence of catalytically effective nickel, noble metals and compounds thereof, (i.e., nickel, rhodium, palladium, silver, osmium, iridium, platinum and gold) to minimize the deleterious catalytic effects thereof. These metals, when contacted with methane at the temperatures employed in the methane contacting step of the present invention, tend to promote coke formation, and the metal oxides tend to promote the formation of combustion products rather than the desired hydrocarbons. The term "catalytically effective" is used herein to identify the quantity of one or more of nickel and the noble metals and compounds thereof which substantially changes the distribution of products obtained in the method of this invention relative to such contacting in the absence of such metals and compounds thereof.

In carrying out the methane conversion reaction, operating temperatures are generally within the range of about 300° to about 1200° C.

The temperature selected may depend in part on the particular reducible metal oxide(s) employed. Best results for contact solids containing manganese have been found at operating temperatures within the range of about 800° to 900° C.

The methane containing hydrocarbon feedstock employed in the process of this invention may contain in addition to methane other hydrocarbon or non-hydrocarbon components. The methane content of the hydrocarbon portion of the feedstock, however, will typically be within the range of about 40 to 100 vol. %, preferably within the range of about 80 to 100 vol. %, more preferably within the range of about 90 to 100 vol. %.

Where gaseous oxidant is cofed, the oxidant preferably comprises a gas containing molecular oxygen (e.g., air). However, oxides of nitrogen, esp. N₂O, have also been found to be effective gaseous oxidants. See U.S. Pat. No. 4,547,610, the entire content of which is incorporated herein by reference.

The ratio of hydrocarbon feedstock to oxygen-containing gas is not narrowly critical to the present invention. Generally, it is desirable to control the hydrocarbon/oxygen molar ratio to avoid the formation of gaseous mixtures within the flammable region. Preferably, the ratio is maintained within the range of about 0.1–300:1, more preferably within the range of about 1–150:1. Methane/air feed mixtures containing about 30 to 90 volume % methane have been found to comprise a desirable feedstream. Further dilution of the feedstream with gases such as nitrogen may be beneficial for improved temperature control.

The provision of added water during at least a portion of the methane/solid contacting is advantageous as described in copending applications Ser. Nos. 07/014,405 and 07/014,406, each filed Feb. 13, 1987. Preferably, the mole ratio of added water to methane in the gas to be contacted is less than about 10. More preferably, this mole ratio is in the range of about 0.01 to about 6, still more preferably about 0.05 to about 4.0. The added water may be combined with the methane-containing gas and/or the oxygen-containing gas prior to contacting the nonacidic solid. For example, the methane-containing gas or the oxygen-containing gas may be contacted with water so that the gas "picks-up" a predetermined, controlled amount of added water prior to the methane/solid contacting. Alternately, a predetermined, controlled amount of water e.g., steam, can be injected into the methane-containing gas and/or the oxygen-containing gas and/or directly into the methane/solid contacting zone or zones.

Operating pressures are not critical to the presently claimed invention. However, both general system pressure and partial pressures of methane and water have been found to effect overall results. Preferred general system pressures are within the range of about 0.1 to 30 atmospheres.

The space velocity of the gaseous reaction streams are similarly not critical to the presently claimed invention, but have been found to effect overall results. Preferred total gas hourly space velocities are within the range of about 100 to 300,000 hr.$^{-1}$, more preferably within the range of about 600 to 100,000 hr.$^{-1}$.

Contacting methane and a reducible metal oxide to form higher hydrocarbons from methane also produces coproduct water and reduces the metal oxide. The exact nature of the reduced metal oxides are unknown, and so are referred to as "reduced metal oxides". Regeneration of reducible metal oxides in the method of the present invention occurs "in situ"—by contact of the reduced metal oxide with the oxygen cofed with methane to the contact zone, or during the oxidizing gas contact part of the redox cycle.

The solids may be maintained in the contact zone as fixed, moving, or fluidized beds of solids. A fixed bed of contact solids is currently preferred for the method of this invention.

The effluent from the contact zones contains higher hydrocarbon products (e.g., ethylene, ethane and other light hydrocarbons), carbon oxides, water and unreacted hydrocarbons (e.g., methane). Higher hydrocarbons may be recovered from the effluent and, if desired, subjected to further processing using techniques known to those skilled in the art. Unreacted methane may be recovered and recycled to the contact zone.

The following examples illustrate the invention.

EXAMPLE 1

An oxidative synthesizing agent catalyst was prepared by mixing (in a ball mill) manganese dioxide (33.2 grams), boric acid (11.8 grams), lithium hydroxide (4.6 grams) and magnesium oxide (43.1 grams) corresponding to an atomic ratio of Li/B/Mn/Mg of about 0.5/0.5/1.0/2.8. Silicon dioxide was added in the amount of 6.5 wt % of the final composition as binder and the mixture was calcined at 900° C. for 16 hours in air.

The calcined catalyst was then treated with hydrogen in order to improve the charactertistics thereof. Specifically, the catalyst was heated to 950° C. and a gaseous stream of 10% hydrogen in argon was passed therethrough at 0.36 ft/sec. After 3 hours treatment the flow of hydrogen was discontinued and the catalyst cooled to 700° C. After an N₂ purge, air was passed through the catalyst for about 2 hours in order to reoxidize the metal oxide to the higher oxidation state, air flow rate being controlled to prevent the catalyst temperature from rising above 800° C.

As a result of this hydrogen treatment bulk density of the catalyst increased from 0.8 to 1.6 g/cc. A sample of catalyst was sieved to 80–140 mesh and the percentage attrition determined after 5 hours at room temperature by passing air therethrough. The weight loss after 5 hours was 4.5%. On a comparable basis, the same catalyst but without the hydrogen treatment showed an attrition weight loss of 24.8%.

A portion of the catalyst was sized to 14–30 mesh size and 5.23 grams were changed to an alumina reactor tube of 0.5 inch inside diameter surrounded by a tubular furnace. The reactor temperature was raised and methane was passed downwardly through the fixed bed of oxidative synthesizing agent and reacted to form higher hydrocarbons in a cyclic redox mode of operation in an extended life testing program. Specifically, methane was passed through the catalyst for 30 seconds at a methane WHSV of 0.75 hrs.$^{-1}$ followed by a nitrogen purge and then reoxidation with air before the cycle was repeated. Cycle time ranged from 7 to 11 minutes, reaction temperature was 825° C., methane GHSV was 1200 hr.$^{-1}$, and methane WHSV was 0.75 hr.$^{-1}$.

After more than 7,800 cycles, catalyst performance had declined from initial methane conversion of 25% and selectivity of conversion to $C_2$+hydrocarbons of 75% to 19% conversion and about 69% selectivity to $C_2$+hydrocarbons.

Lithium metaborate (LiBO₂) was added to the catalyst bed during the oxidation portion of the cycle by introduction of LiBO₂ powder with the oxidant gas, the amount added being 1.4 wt % of the catalyst expressed as Li and the life tests were continued. At the 12500 cycle mark performance was 22% methane conversion with 81% selectivity to $C_2$+hydrocarbons.

We claim:

1. In a process for the conversion of methane to higher hydrocarbons and coproduct water wherein methane is contacted at reactive conditions with a conversion catalyst comprised of a reducible metal oxide selected from the group consisting of an xoide of manganese, tin, indium, germanium, antimony, leads, bismuth, cerium, praseodymium, terbium, iron, and rutheium, the improvement which comprises pretreating the catalyst before use in the conversion of methane to higher hydrocarbons and coproduct water with a reducing agent at 650° C. to 1200° C. for a time sufficient to improve the bulk density and attrition resistance of the said catalyst and thereafter contacting the pretreated catalyst with methane at methane conversion conditions effective to form higher hydrocarbons and coproduct water.

2. The process of claim 1 wherein said catalyst is treated with 0.5 to 20 times the stoichiometric quantity of reducing agent.

3. The process of claim 1 wherein said catalyst is treated with a reducing agent at 850° C. to 1000° C.

4. The process of claim 1 wherein said catalyst is treated with 0.5 to 10 times the stoichiometric quantity of reducing agent.

5. The process of claim 1 wherein the reducible metal oxide comprises manganese.

6. In a process for the conversion of methane to higher hydrocarbons and coproduct water wherein methane is contacted with a conversion catalyst comprised of a reducible metal oxide selected from the group consisting of an oxide of manganese, tin, indium, germanium, antimony, lead, bismuth cerium, praseodymium, terbium, iron, and ruthenium, the improvement which comprises pretreating the catlayst before use in the conversion of methane to higher hydrocarbons and water with a reducing agent at 650° C. to 1200° C. with 0.5 to 20 times the stoichiometric quantity of reducing agent, reoxidizing the treated catalyst to a higher oxidation state, and thereafter contacting the pretreated catalyst with methane at methane conversion conditions effective to form higher hydrocarbons and coproduct water.

7. The process of claim 6 wherein the treated catalyst is reoxidized with $O_2$.

8. The process of claim 6 wherein the treated catalyst is reoxidized at 350° C. to 1200° C.

9. The process of claim 6 wherein the treated catalyst is reoxidized at 500° C. to 1000° C.

10. The process of claim 6 wherein the treated catalyst is reoxidized at a temperature no higher than 850° C.

11. In a process for the conversion of methane to higher hydrocarbons and coproduct water wherein methane is contacted at reactive conditions with a conversion catalyst comprised of a reducible metal oxide selected from the group consisting of an oxide of manganese, tin, indium, germanium, antimony, lead, bismuth, cerium, praseodymium, terbium, iron, and ruthenium, the improvement which comprises pretreating the catalyst before use in the conversion of methane to higher hydrocarbons and coproduct water with 0.5 to 20 times the stoichiometric quantity of hydrogen at 650° C. to 1200° C. and thereafter contacting the pretreated catalyst with methane at methane conversion conditions effective to form higher hydrocarbons and coproduct water.

* * * * *